(12) United States Patent
Roe et al.

(10) Patent No.: US 7,432,413 B2
(45) Date of Patent: Oct. 7, 2008

(54) DISPOSABLE ABSORBENT ARTICLE HAVING SIDE PANELS WITH STRUCTURALLY, FUNCTIONALLY AND VISUALLY DIFFERENT REGIONS

(75) Inventors: Donald Carroll Roe, West Chester, OH (US); Barry Robert Feist, Cincinnati, OH (US); Krista Beth Comstock, Mason, OH (US); Lisa Jane Goodlander, White Oak, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 11/303,686

(22) Filed: Dec. 16, 2005

(65) Prior Publication Data

US 2007/0142806 A1 Jun. 21, 2007

(51) Int. Cl.
*A61F 13/15* (2006.01)

(52) U.S. Cl. ............... 604/378; 604/379; 604/380; 604/381; 604/382; 604/383

(58) Field of Classification Search ............ 604/378, 604/379, 380, 381, 382, 383
See application file for complete search history.

(56) References Cited

U.S. PATENT DOCUMENTS

| | | | |
|---|---|---|---|
| 4,856,504 A | 8/1989 | Yamamoto et al. | |
| 4,861,652 A | 8/1989 | Lippert et al. | |
| 4,916,005 A | 4/1990 | Lippert et al. | |
| 4,938,753 A | * 7/1990 | Van Gompel et al. | .. 604/385.29 |
| 5,234,423 A | 8/1993 | Alemany et al. | |
| 5,571,096 A | * 11/1996 | Dobrin et al. | ............ 604/383 |
| 5,580,411 A | 12/1996 | Nease et al. | |
| 5,683,533 A | 11/1997 | Keighley et al. | |
| 5,705,013 A | 1/1998 | Nease et al. | |
| 5,797,824 A | 8/1998 | Tracy | |
| 5,947,946 A | 9/1999 | Fisher et al. | |
| 6,117,121 A | 9/2000 | Faulks et al. | |
| 6,132,411 A | 10/2000 | Huber et al. | |
| 2003/0100878 A1 | 5/2003 | Leak et al. | |
| 2003/0109844 A1 | 6/2003 | Gibbs | |
| 2005/0215972 A1 | 9/2005 | Roe et al. | |

(Continued)

FOREIGN PATENT DOCUMENTS

EP 433951 A2 12/1990

(Continued)

OTHER PUBLICATIONS

International Search Report.

(Continued)

*Primary Examiner*—Jacqueline F. Stephens
(74) *Attorney, Agent, or Firm*—Jay Krebs; Thibault Fayette; Matthew P. Fitzpatrick

(57) ABSTRACT

A disposable absorbent article worn about the lower torso of a wearer includes at least one pair of side panels connecting a first waist region to a second waist region forming a waist opening and a pair of leg openings. Each side panel includes a waist region, a hip region and a leg region wherein the waist region, the hip region and the leg region differs structurally, functionally and visually to provide an improved initial fit and sustained fit while exhibiting a garment-like appearance.

5 Claims, 5 Drawing Sheets

U.S. PATENT DOCUMENTS

| | | |
|---|---|---|
| 2005/0215973 A1 | 9/2005 | Roe et al. |
| 2007/0142798 A1 | 6/2007 | Goodlander et al. |
| 2007/0142815 A1 | 6/2007 | Macura et al. |

FOREIGN PATENT DOCUMENTS

| | | |
|---|---|---|
| WO | WO01/87213 A1 | 11/2001 |
| WO | WO01/87214 A1 | 11/2001 |
| WO | WO01/87588 A2 | 11/2001 |
| WO | WO02/13747 A1 | 2/2002 |

OTHER PUBLICATIONS

U.S. Appl. No. 11/303,306, filed Dec. 16, 2005, Goodlander et al.
U.S. Appl. No. 11/303,687, filed Dec. 16, 2005, Macura et al.

* cited by examiner

DISPOSABLE ABSORBENT ARTICLE HAVING SIDE PANELS WITH STRUCTURALLY, FUNCTIONALLY AND VISUALLY DIFFERENT REGIONS

FIELD OF THE INVENTION

This invention is directed to hygienic absorbent articles, such as diapers, pant style diapers, training pants and the like. Particularly, the invention is directed to such hygienic absorbent articles having side panels including regions that differ structurally, functionally and visually.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing.

Diaper manufacturers have attempted to improve the appearance and function of diapers by providing a more garment like look and improving fit by introducing stretch. However, often times the features influencing fit adversely affect the appearance. For instance, disposable diapers with side stretch features have used stretch and force profiles to provide good initial fit as well as good sustained fit. Disposable diapers offering such side stretch features are often multipiece designs composed of diaper chassis with stretchable side panels bonded to and extending from at least one of the longitudinal side edges. Such multipiece designs often appear less garments-like and require decorative features to compensate. In addition, the bond extending parallel to the longitudinal side edges of the diaper causes forces to be very similar or equal along the stretch panel from top to bottom when the diaper is applied on a wearer. The equal forces result in either red marking of the skin at the top of the leg, poor sustained fit about the waist, or both. In addition, the edges of the side panels tend to fold or roll inward toward the center of the side panel exhibiting a poor fit that appears less garment-like.

Therefore, it is an object of the present invention to provide a disposable absorbent article capable of providing improved initial fit, sustained fit, and reduced red marking of the wearer's skin while appearing more garment-like.

SUMMARY OF THE INVENTION

The present invention provides a disposable absorbent article to be worn about the lower torso of a wearer. The disposable absorbent article includes at least one pair of side panels connecting a first waist region to a second waist region forming a waist opening and a pair of leg openings. Each side panel includes a waist region, a hip region and a leg region wherein the waist region, the hip region and the leg region differ structurally, functionally and visually to provide an improved initial fit and a sustained fit while exhibiting a garment-like appearance.

In one embodiment, a pair of side panels is disposed in the second waist region. Each side panel includes a waist region, a hip region and a leg region, where the waist, hip and leg regions differ structurally, functionally and visually. Each side panel also includes a fastener for releasably attaching the side panel to the first waist region.

In another embodiment, a first pair of side panels is attached to the second waist region and second pair of side panels is attached to the first waist region. The first pair of side panels is attached to the second pair of side panels forming a pant having a waist opening and a pair of leg openings. Each pair of side panels includes a waist region, a hip region and a leg region wherein the waist region, hip region and the leg region differ structurally, functionally, and visually.

BRIEF DESCRIPTION OF THE DRAWINGS

While this specification concludes with claims particularly pointing out and distinctly claiming that which is regarded as forming the present invention, it is anticipated that the invention can be more readily understood through reading the following detailed description of the invention and study of the accompanying drawings.

DETAILED DESCRIPTION OF THE INVENTION

Definitions

Figure 1:
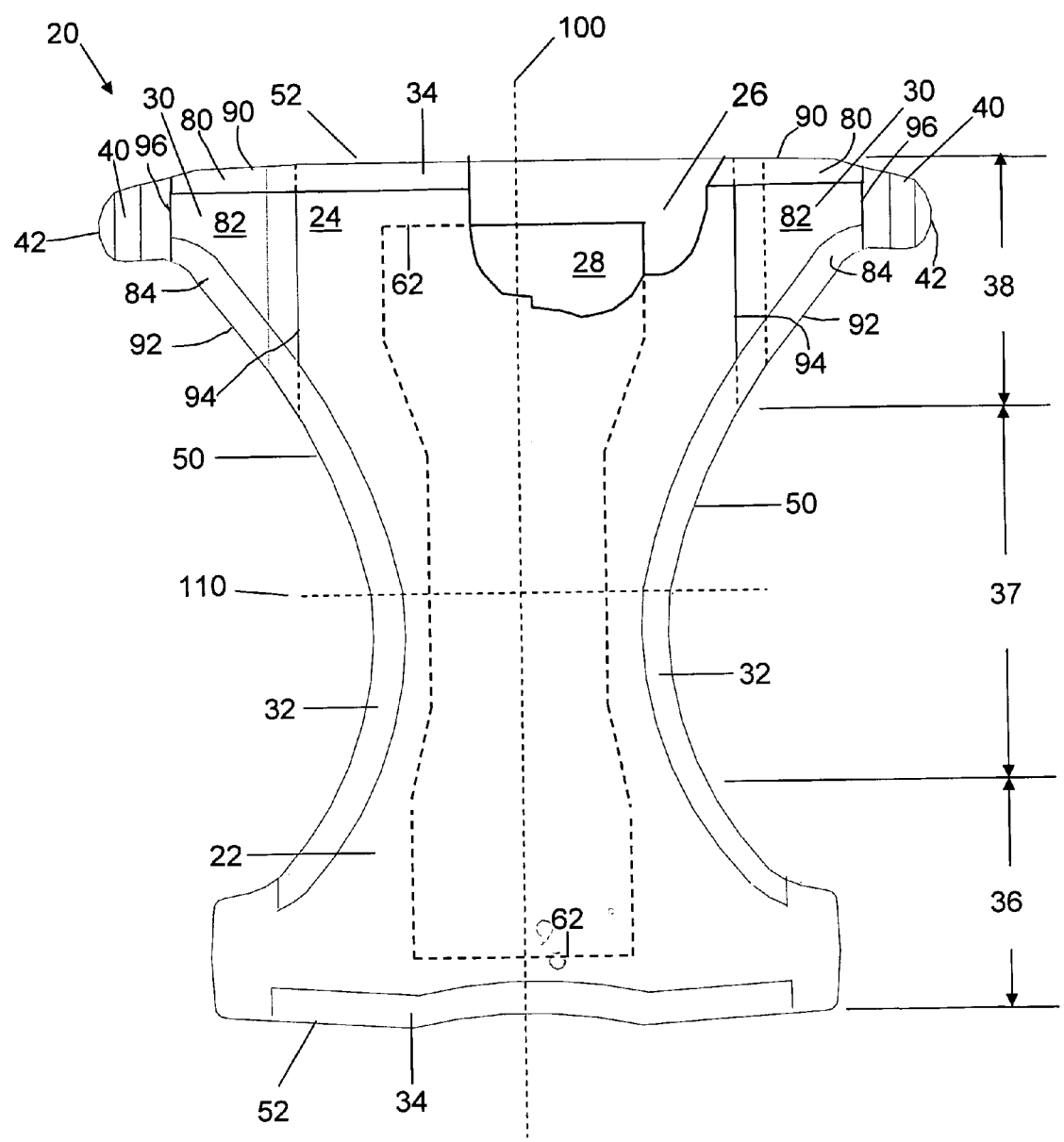
FIG. 1 is a plan view of a disposable diaper constructed in accordance with the present invention having portions cut away to reveal underlying structure. The body-facing surface of the diaper is facing the viewer.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The "x-y plane refers to the plane congruent with the longitudinal and transverse directions.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

The terms "permeable" and "impermeable" refer to the penetrability of materials in the context of the intended usage of disposable absorbent articles. Specifically, the term "permeable" refers to a layer or a layered structure having pores or openings that permit liquid water to pass through its thickness in the absence of a forcing pressure. Conversely, the term "impermeable" generally refers to articles and/or elements that are not penetrative by fluid through the entire Z-directional thickness of the article under pressure of 0.14 lb/in$^2$ or less. Preferably, the impermeable article or element is not penetrative by fluid under pressures of 0.5 lb/in$^2$ or less. More preferably, the impermeable article or element is not penetrative by fluid under pressures of 1.0 lb/in$^2$ or less.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently. The term "attached" includes elements which are integrally formed with another element.

The terms "corrugations" or "rugosities" are used to describe hills and valleys that occur in a substrate or in a laminated structure. Neither term, i.e. "corrugations" nor "rugosities", mandates that either the hills or valleys created are uniform in nature.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner).

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "stretch" means to forcibly extend in length or width.

"Live stretch" includes stretching elastic and bonding the stretched elastic to a nonwoven. After bonding the stretched elastic is released causing it to contract, resulting in a "corrugated" nonwoven. The corrugated nonwoven can stretch as the corrugated portion is pulled to about the point that the nonwoven reaches at least one original flat dimension. The elastic is preferably stretched at least 25% and more preferably at least 100% of its relaxed length when it is bonded to the nonwoven.

The terms "pant", "pant style diaper", "training pant", "closed diaper", "pre-fastened diaper", and "pull-on diaper", as used herein, refer to disposable garments having a waist opening and leg openings designed for infant or adult wearers. A pant can be configured such that the pant has a closed waist and leg openings prior to being donned on the wearer or the pant can be configured such that the waist is closed and the leg openings are formed while on the wearer. A pant may be preformed by any suitable technique including, but not limited to, attaching together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

Description

Wearable articles constructed in accordance with the present invention have a pair of side panels where each side panel includes regions that differ visually, structurally or functionally. The side panels are equally applicable to wearable articles such as disposable absorbent articles including diapers, pant style diapers, training pants, incontinence briefs, incontinence undergarments, absorbent inserts, diaper holders and liners, feminine hygiene garments, and the like. One embodiment of an absorbent article of the present invention is a unitary disposable absorbent article, such as the diaper 20, shown in FIG. 1.

FIG. 1 is a plan view of the diaper 20 of the present invention in a flat-out state with portions of the structure being cut-away to more clearly show the construction of the diaper 20. The portion of the diaper 20 which faces the wearer is oriented towards the viewer. The diaper 20 has a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

As shown in FIG. 1, the diaper 20 comprises a liquid pervious topsheet 24; a liquid impervious backsheet 26; an absorbent core 28 which is preferably positioned between at least a portion of the topsheet 24 and the backsheet 26; side panels 30; extensible leg cuffs 32, elastic waist features 34 and a fastening system generally designated 40. The chassis 22 of the diaper 20 comprises the main body of the diaper 20 and includes the topsheet 24 and/or the backsheet 26 and at least a portion of the absorbent core 28. While the topsheet 24, the backsheet 26, the absorbent core 28, side panels 30 and other aforementioned constituents may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method for Manufacturing Side Panels for Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999.

The side panels 30 can have a number of different sizes and shapes, but preferably have a trapezoidal shape. The side panels 30 can be elastic or extensible to provide a more comfortable and contouring fit by initially conformably fitting the diaper 20 to the wearer and sustaining this fit throughout the time of wear. Side panels 30 which are elasticized can provide a sustained fit well past when the diaper 20 has been loaded with exudates since the elasticized side panels 30 allow the sides of the diaper 20 to expand and contract. The side panels 30 may also provide more effective application of the diaper 20 because even if one elasticized side panel 30 is pulled farther than the other during application, the diaper 20 will "self-adjust" during wear.

The side panels 30 may comprise a separate element affixed to the chassis 22, or can be constructed as an extension of other elements of the diaper such as the backsheet 26 or the topsheet 24, preferably both the topsheet 24 and the backsheet 26. In the embodiment shown in FIG. 1, the side panels 30 each comprise a separate web joined to the chassis 22 in the second waist region 38 and extend laterally outwardly beyond the longitudinal edges 50. The side panels 30 comprise a first end edge 90 positioned adjacent the end edge 52 of the diaper, a second end edge 92 positioned away from the first end edge 90 towards the lateral centerline 110, a first longitudinal edge 94 attached to the longitudinal edge 50, and a second longitudinal edge 96 positioned laterally outwardly from the longitudinal edge 50. The first longitudinal edge 94 may be contiguous with the longitudinal edge 50, preferably the first longitudinal edge 94 is positioned laterally inwardly of the longitudinal edge 50. The side panels 30 may include a non-elastic extension members 42 attached to the second longitudinal edges 96 and fasteners 40 attached to the nonelastic extension members 42. The nonelastic extension members 42 can be made to distribute the shear forces along the second longitudinal edges 96 of the side panels 30 during fastening.

While the diaper 20 shown in FIG. 1 has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; and U.S. Pat. No. 6,004,306 entitled "Absorbent Article With Multi-Directional Extensible Side Panels" issued to Robles et al. on Dec. 21, 1999.

Figure 2:
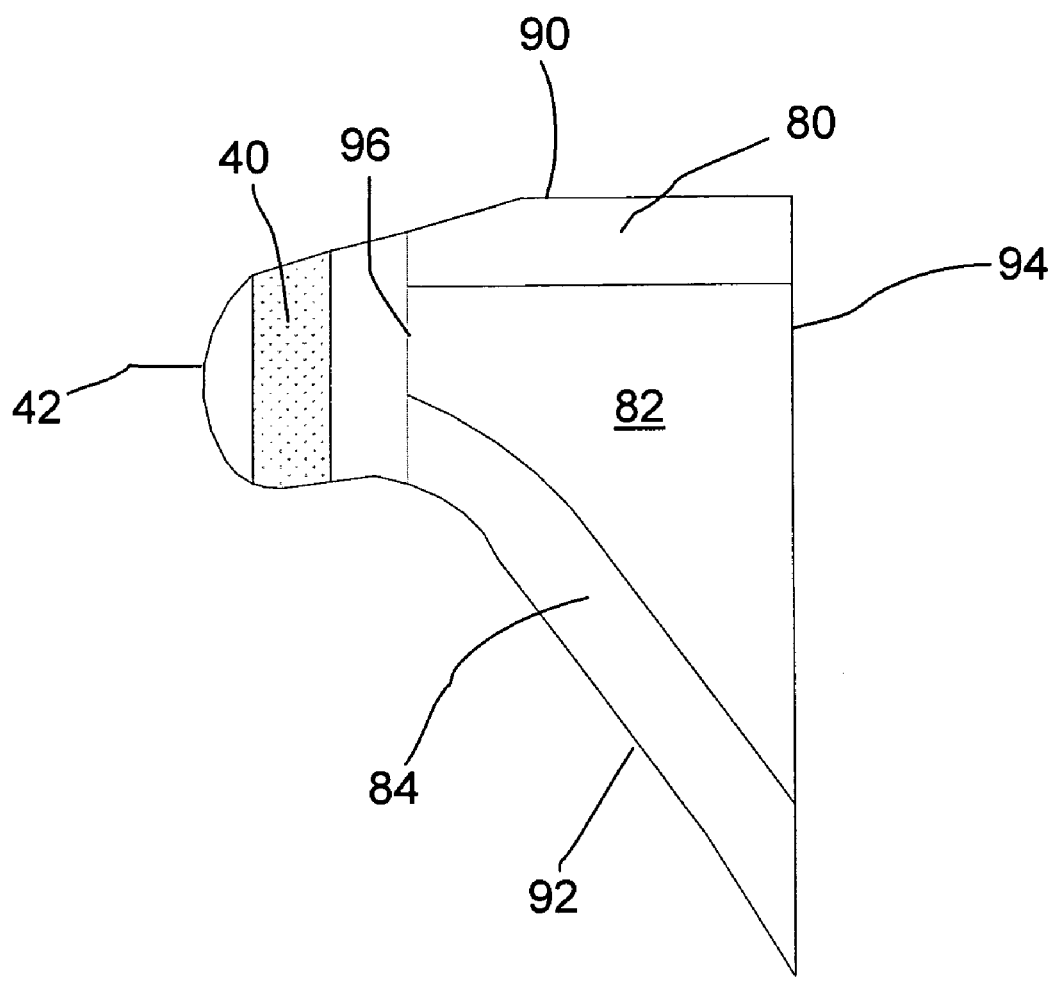
FIG. 2 is a plan view of side panel attached to the disposable diaper in FIG. 1.

The side panels 30 of the present invention include separate regions where each region differs structurally, functionally or visually. For instance, the side panel shown in FIG. 2 includes three regions, a waist region 80, a hip region 82 and a leg region 84. The waist region 80 is located near end edge 52 and can extend from the first longitudinal edge 94 to the second longitudinal edge 96. The leg region 84 is located near the longitudinal edge 50 and can extend from the first longitudinal edge 94 to the second longitudinal edge 96. The hip region 82 is located between the waist region 80 and the leg region 84 and can extend from the first longitudinal edge 94 to the second longitudinal edge 96. The area of the side panel 30 occupied by each of the regions may vary; however, the hip region can cover 40%-90%, preferably 60%-80% of the side panel surface area, while the waist region can cover, 5%-30%, preferably 10%-20% of the side panel surface area and the leg region can cover, 5%-30%, preferably 10%-20% of the side panel surface area.

Each of the waist, hip and leg regions 80, 82, 84 can differ from the other two regions either structurally, functionally or visually. In one embodiment, each of the three regions differs from the other two regions structurally and visually. In another embodiment, each of the three regions can differ from the other two regions functionally and visually. In another embodiment, each of the three regions can differ from the other two regions structurally and functionally. In yet another embodiment, each of the three regions can differ from the other two regions structurally, functionally, and visually. Further, in another embodiment, any two regions may be the same but differ from the third region structurally, functionally or visually. In still another embodiment, any two regions may be structurally, functionally, and visually the same but differ from the third region structurally, functionally and visually.

Structural differences between the waist region 80, hip region 82, and leg region 84 can include differences in types of materials used; activation patterns in zero-strain elastomeric laminates; material thicknesses; bonding patterns; layers of materials and combinations thereof. Structural differences between the waist region 80, hip region 82, and leg region 84 of the side panel 30 can be made to accentuate the visual distinctiveness between the regions, affect the functional attributes of the regions or both.

Functional differences between the waist region 80, hip region 82, and leg region 84 of the side panel 30 can be made to influence how the diaper 20 fits on a wearer. Functional differences can include differences in stiffness, bending modulus, elastic modulus, extensibility, force relaxation, set, recovery rate, torsional modulus, compression modulus, compressibility, coefficient of friction, surface energy and combinations thereof.

The side panels 30 may be constructed from a number of different materials. For instance, the side panels may comprise conventional elastic materials or stretch laminates. The stretch laminates may comprise a laminated structure known as live stretch, previously defined, where an elastic element is attached to a substrate while the elastic element is under strain; such that once the strain is relieved the laminate forms corrugations or gathers and exhibits a shirred structure having elastic-like properties.

Alternatively, the stretch laminate may comprise a mechanically activated stretched laminate such as a zero strain stretch laminate. Zero strain stretch laminates comprise a laminated structure which includes a first substrate, a second substrate and an elastic element. The first substrate and the second substrate, which are typically non-elastic nonwovens, are attached to the elastic element in a face to face orientation such that the elastic element is sandwiched between the first substrate and the second substrate. The laminated structure is mechanically activated enabling it to stretch. Mechanical activation refers to a process wherein the nonwoven fibers of the non-elastic substrates are broken, and/or stretched, within the nonwoven so that the nonwoven is stretched in a direction along its surfaces and can be easily expanded in that direction by partial straightening of the fibers in the nonwoven. Zero-strain elastomeric laminates are described in U.S. Pat. No. 5,143,679 issued to Weber et al., U.S. Pat. No. 5,156,793 issued to Buell et al., and U.S. Pat. No. 5,167,897 issued to Weber.

The elastic element used in the side panels 30 can include elastic strands or elastic films. Any suitable elastic film known in the art can be used. Suitable elastic films may comprise polypropylene, polyethylene, polyolefins, styrene-isoprene-styrene, styrene-butadiene-styrene, or combinations thereof. The basis weight of the films can range from about 10 gsm to about 100 gsm.

Suitable elastic strands can be made of a resilient elastic thermoplastic material. The elastic strands may be made from liquid elastic that is extruded through a die to achieve the desired strand elastic diameter and/or shape. The shape of the extruded elastic strands is not limited. For example, typical elastic strands have a circular cross sectional shape, but sometimes the elastic strands may have different shapes, such as a trilobal shape, or a flat (i.e., "ribbon" like) shape. Suitable elastic strand shapes include rectangles, circles, ellipses, diamonds, triangles, parallelograms, trapezoids, wedges or other sections of circles or ellipses, other polygons, or other irregular enclosed shapes. Furthermore, the thickness or diameter of the elastic strands may vary in order to accommodate a particular application. Typically, the thickness of elastic strands may be in the range of about 0.02 mm to about 1 mm and the basis weight is in the range of about 20 g/m$^2$ to about 300 g/m$^2$.

The elastic strands can be adhesively attached to the substrate, extruded onto the substrate, or printed onto the substrate. Suitable apparatuses for applying elastic strands in a longitudinal direction are described in U.S. Publication No. 2004/0238105 A1 and in U.S. application Ser. No. 10/836,944 entitled "Apparatus for Producing Elastomeric Nonwoven Laminates" filed on Apr. 30, 2004. Apparatuses for applying elastic strands in a transverse direction, an angle from the longitudinal direction, or in a curvilinear fashion are described in U.S. Publication No. US 2005-0178494 A1 entitled "Method of Placing Material Transversely on a Moving Web" filed on Feb. 13, 2004. Apparatuses for applying elastic strands in the longitudinal direction, an angle from the longitudinal direction, or in a curvilinear fashion are described in U.S. application Ser. No. 10/834,539 entitled "Extrusion Applicator Having Linear Motion Operability" filed on Apr. 29, 2004, and in U.S. application Ser. No. 10/834,503 entitled "Extrusion Applicator Having Rotational Operability" filed on Apr. 29, 2004.

Suitable apparatuses and methods for printing elastic elements in any orientation are described in U.S. Publication No. 2004-0181200A1 entitled "Variable Stretch Composites and Methods of Making the Composite" filed on Mar. 29, 2004, and in U.S. Publication No. 2004-0193133A1 entitled "Variable Stretch Composites and Methods of Making the Composite" filed on Mar. 29, 2004. For the printing of elastic strands, the individual elastic strands may be configured as lines or strands generally having widths less than about 2 mm and typically less than about 1 mm. Linear elastic strands may be configured as bands generally having widths between about 2 mm and about 20 mm and aspect ratios ranging from about 2:1 to about 100:1. Typically, the thickness of an elastic strand may be in the range of about 0.02 mm to about 5 mm and the basis weight is in the range of about 20 g/m$^2$ to about 300 g/m$^2$.

The first or second substrates forming the side panels may comprise woven materials, nonwoven materials, combinations of woven and nonwoven materials, or laminated structures having woven or nonwoven materials. Suitable nonwoven materials for use in accordance with the present invention may comprise fibers made of polypropylene, polyethylene, polyester, nylon, cellulose, polyamide, or combinations of such materials. Fibers of one material or fibers of different materials or material combinations may be used in the nonwovens. Suitable processes for manufacturing nonwoven materials include spunbond, spunbond meltblown spunbond (SMS), spunbond meltblown meltblown spunbond (SMMS), carded and the like. Other suitable nonwoven materials include high elongation carded (HEC) nonwovens and deep activation polypropylene (DAPP) nonwovens. Any process known in the art may be used to make the nonwovens. The basis weight of the first nonwoven and/or second nonwoven may, for example, be in the range of about 10 gsm to about 40 gsm.

The first substrate, second substrate and the elastic element may be attached by any means of attachment known in the art. Suitable attaching means and/or methods for attaching include, but are not limited to, adhesives, cohesives, thermal bonding, pressure bonding, mechanical bonding, ultrasonic bonding, and/or any combination of any known methods of attaching such materials.

Structural differences between the waist region 80, hip region 82, and leg region 84 of the side panels 30 may include the use of different elastomeric elements in the waist region 80 and/or leg region 84 versus the hip region 82 resulting in differences in functional properties and visual appearance based on the properties of the individual materials. For instance, a zero-strain elastomeric laminate side panel may include elastic elements attached under tension to the waist region 80 and leg region 84 of the side panels 30 producing a greater number of rugosities which are greater in size when relaxed than zero-strain stretch laminates in the hip region 82 causing visual distinctions which make them appear as garment-like seams while at the same time provide gripping or applications aids. Alternatively, different activation patterns among the regions may yield visually different regions with different maximum elongations and/or stress/strain properties. Likewise, variations in bonding patterns between layers in the regions may affect the stress/strain properties and the frequency and/or size of rugosities in the region.

Other Examples of side panels 30 constructed with a structurally different waist region 80, hip region 82, and leg region 84 resulting in functional differences among the regions and methods of forming the same are provided below.

In one embodiment, the structural differences may result in the elastic modulus of the hip region 82 being higher than elastic modulus of the waist and/or leg regions 80, 84, enabling the hip region 82 to carry more of the anchoring load. This can lead to reduced marking and reduced tendency of any attached fastener to curl under side panel tension. Alternatively, the elastic modulus may be higher in the waist and/or leg regions 80, 84 versus the hip region 82 if increased gasketing or perimeter edge control is required.

In another embodiment, the structural differences may involve extensibility where the extensibility of the waist and/or leg regions 80, 84 may be greater than that of the hip region 82 so as to allow the waist and legs to move freely without binding, reducing the potential for red marking. Alternatively, the waist and/or leg regions 80, 84 may be less extensible than the hip region 82 to better gasket and protect against waste leakage.

Differences in the elastic modulus and stretchability between the waist, hip and leg regions 80, 82, 84 can be affected by including structural differences in the regions impacting these properties.

For instance, a zero strain stretch laminate side panel can be mechanically activated by meshing the side panel between first and second activation rolls each of which comprises a plurality of teeth. The teeth of the first activation roll intermesh with the teeth of the second activation roll. Structural differences between the waist hip and leg regions 80, 82, 84 can be attained by mechanically activating portions of the side panel to different percentages of strain. The percentage strain experienced by the side panel regions depends on the depth of engagement between the intermeshing teeth of the first activation roll and the teeth of the second activation roll. Activating portions of the side panel at smaller depths of engagement (e.g. shorter teeth) results in different functional characteristics as compared to portions activated at larger depths of engagement. The portions exposed to the smaller depths of engagement experience smaller percentages of strain making them less elastically extensible. For example, a portion of a side panel which was strained to 200% may be able to elastically extend up to about three times its original length. However, a portion which was strained to 500% may be able to elastically extend up to about six times its original length.

In an alternate embodiment, a side panel may comprise a plurality of elastic elements attached to a substrate. The functional differences can be attained by altering the spacing of the plurality of elastic elements. For example, the spacing between each of the of elastic elements in the waist region 80 and the leg region 84 may be about 2 mm while the spacing between each of the plurality of elastic elements in the hip region 82 may be about 1 mm. Alternatively, the spacing between each of the elastic elements in the waist region 80, leg region 84 and waist region 82 can differ. For instance, the spacing between the elastic elements in the waist region 80 may be 1 mm, while the spacing between the elastic elements in the hip region 82 is 2 mm and the spacing between the elastic elements in the leg region is 3 mm. Assuming the plurality of elastic elements has the same physical and chemical properties in the waist, leg, and the hip regions 80, 84, 82, the elastic modulus in each of the regions can differ relative to the spacing.

In another embodiment, structural differences resulting in functional differences such as elastic modulus and/or stretchability can be attained by altering the properties of a plurality of elastic elements. For instance, a plurality of elastic elements in the waist region 80, can have different physical or chemical properties than the physical or chemical properties of a plurality of elastic elements in the leg region 84 and both the waist and leg regions 80, 84 can have different physical or chemical properties than the physical or chemical properties of a plurality of elastic elements in the in a hip region 82. For instance, a plurality of elastic elements in the waist region 80 may have a smaller cross sectional area than a plurality of elastic elements in the hip region 82 but larger cross sectional area than a plurality of elastic elements in the leg region 84. For example, where the elastic elements comprise elastic strands, the cross sectional area of the plurality of elastic elements in the waist region 80, can vary from about 0.03 $mm^2$ to about 0.1 $mm^2$. In contrast, the cross sectional area of the plurality of elastic elements in the hip region 82 can be greater than about 0.1 $mm^2$ and less than or equal to about 0.4 $mm^2$, and the cross sectional area of the plurality of elastic elements in the leg region 84 can be less than about 0.03 $mm^2$ thereby providing the hip region 82 with a higher elastic modulus than the waist and leg regions 80, 84 and a waist region 82 with a higher elastic modulus than the leg region 84.

In another embodiment, the structural differences impacting different elastic modulus and stretchability between the regions may include providing a region with additional elastic elements impacting the function of that region. For example, a side panel 30 may comprise an elastic element which is present in the waist region, 80 hip region 82 and leg region 84. In order to impact the functionality of the hip region 82, an additional elastic element may be added to the hip region 82 such that its functional properties differ with respect to the waist and leg regions 80, 84. Alternatively, an additional elastic element may be added to the waist or leg regions 80, 84 or both and not the hip region 82.

At this point, it is worth noting that any of the aforementioned methods for producing structural differences and corresponding functional differences can be combined to provide the desired properties in a side panel 30.

Another embodiment where the functional differences between the waist, hip and leg regions 80, 82, 84 of the side panel 30 are attained by structural differences includes increasing the bending modulus and corresponding stiffness of the waist and/or leg region 80, 84 over the bending modulus and corresponding stiffness of the hip region 82 in order to resist the first and second end edges 90, 92 in the waist or leg regions 80, 84 from folding or rolling over while at the same time allowing the hip region 82 to flex and move freely with the wearer, reducing the chance of red marking on the wearer's skin. Bending stiffness can be increased by adding an additional layer to the waist and/or leg regions 80, 84 adding rugosities to waist and/or leg regions 80, 84 via elastic contraction where the rugosities are oriented substantially perpendicular to the longitudinal edges 50 and end edges 52, or increasing the thickness of the existing material.

For another embodiment, the structural differences may result in functional differences such as the force relaxation (set, etc.). For instance, it may be desirable for the force relaxation in the hip region 82 to be lower than force relaxation in the waist and/or leg region 80, 84 to allow the hip region 82 to effectively carry the waist anchoring tension and resist sagging. This may be accomplished by using a high quality elastomer such as a hydrogenated elastomer in the waist and leg regions 80, 84. Hydrogenated elastomers have a lower force relaxation (less hysteresis) than non-hydrogenated elastomers.

In another embodiment the structural differences may impact functional differences such as recovery rate, which is a measure of how rapidly the region returns to an original relaxed length upon removal of a tensile force. For instance, it may be desirable for the recovery rate in the waist and/or leg regions 80, 84, be lower (i.e., slower) than the hip region 82 to aid in fitting the article to the wearer by delaying tight leg/waist fit until after the article is on the wearer. Delayed recovery response may be enabled by slow-recovery elastomers. Slow recovery elastomers are described in U.S. application Ser. No. 11/144,508, filed Jun. 3, 2005, titled "Absorbent Articles Comprising A Slow Recovery Elastomer" and U.S. application Ser. No. 11/144,497, filed Jun. 3, 2005, titled "Absorbent Articles Comprising A Slow Recovery Stretch Laminate".

In another embodiment, the structural differences between the regions can be made to impact the torsional modulus in the regions resulting in a greater torsional modulus in waist and/or leg regions 80, 84 than the torsional modulus of the hip region 82 so as to reduce the tendency of the waist and leg regions to twist. Keeping the regions flat spreads the tension over a greater area rather than concentrating the tension on a narrow area which can cause red marking. Similar to bending stiffness above, torsional modulus can be increased by adding an additional layer to the waist and/or leg regions 80, 84, adding rugosities via elastic contraction to the waist and leg regions where the rugosities are oriented substantially perpendicular to the end edge 52 or longitudinal edge 50, or increasing the thickness of the existing material.

In another embodiment, the structural differences between the regions may impact the compressive modulus. For instance, the compressive modulus of the waist and/or leg regions 80, 84 may be lower than the compressive modulus of the hip region 82. Since the waist and leg regions are along the perimeter of the article, minimizing the compressive modulus in these regions can increase the comfort level along the perimeter of the article. Compressive modulus can be reduced by increasing loft (thickness) of the material at a given basis weight, reducing the inter-layer bond density of laminated or layered structures, or choosing a material having an inherently lower compressive modulus.

In another embodiment, the structural differences among the regions may impact the coefficient of friction resulting in a greater coefficient of friction in the waist and leg regions 80, 84 than that of the hip region 82 so that the waist and leg regions form gaskets with zero or significantly reduced slippage in the waist and leg regions 80, 84. Alternatively, the coefficient of friction in the hip region 82 may be higher than the waist and leg regions 80, 84 to facilitate anchoring and sustained fit of the article on the wearer. COF may be reduced by a) application of a slip agent such as a lotion, a powder, or a low surface energy material such as Teflon or b) use of a smooth material with few micro projections that could "snag" on rugosities in the skin. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997; U.S. Pat. No. 5,609,587 entitled "Diaper Having A Lotion Topsheet Comprising A Liquid Polyol Polyester Emollient And An Immobilizing Agent" issued to Roe on Mar. 11, 1997; U.S. Pat. No. 5,635,191 entitled "Diaper Having A Lotioned Topsheet Containing A Polysiloxane Emollient" issued to Roe et al. on Jun. 3, 1997; U.S. Pat. No. 5,643,588 entitled "Diaper Having A Lotioned Topsheet" issued to Roe et al. on Jul. 1, 1997; U.S. Pat. No. 5,968,025 entitled "Absorbent Article Having a Lotioned Topsheet" issued to Roe et al. on Oct. 19, 1999 and U.S. Pat. No. 6,716,441 entitled "Compositions for the efficient release of active ingredients" issued to Osborne on Apr. 6, 2004.

In another embodiment, the structural differences may affect the functionality of the waist hip and leg regions 80, 82, 84 by influencing the surface energy of one or more of the regions. Surface energy refers to the activity of the surface, such as the positive, negative or zero charge of the surface which affects how other substances interact with the surface. For instance, surface energy can effect how fluids spread on the surface or adhere to the surface. Surface energy differences could result from coating one portion of the ear with a Teflon-like material or silicone coating to provide a barrier to urine while the untreated portion would provide better adherence for ink printing. Examples of coatings affecting surface energy include those described in application Ser. No. 11/055,743 filed Feb. 2, 2005 titled "Hydrophobic Surface Coated Absorbent Articles and Associated Methods".

Structural differences between the waist, hip, and leg regions 80, 82, 84 can also influence visual aspects of the regions. In addition to structure, visual differences between the regions can also be influenced by colors, textures, patterns, thickness, opacity, reflectivity, sheen, rugosity size, rugosity spacing, and rugosity frequency. Visual differences between the waist, hip, and leg regions 80, 82, 84 can contribute to a garment-like appearance and/or provide an aid in fitting the diaper to the wearer.

A garment-like look can be accomplished by making the regions appear cloth-like. For instance, the waist and leg regions 80, 84 of the side panel 30 can be made to look like seams while the hip region 82 is made to appear as a cloth like fabric panel. Such visual distinctiveness can be accomplished by adding color, patterns and/or layers of elastic material producing visible gathers or rugosities via elastic contraction.

In one embodiment, structural differences can be introduced to influence visual differences as well as functional differences. For instance, elastic materials can be prestrained and attached to the waist region 80, hip region 82 and leg region 84 at different levels of strain producing different visible gathers or rugosities to further distinguish the appearance of each of the regions while at the same time provide elastic properties desirable for each of the regions.

In addition, the visual differences between the waist, hip and leg regions 80, 82, 84 can be combined with the aforementioned structural and functional differences in order to a) provide an indication of where to grasp the side panel in order to stretch it during application, b) make the leg and waist regions easier to distinguish to aid in application, c) provide a visually appealing pattern (e.g., racing stripes, etc.) to a child wearer, d) provide an indication of the front vs. the back of the article, e) provide intuitive instructions to the caregiver to facilitate application or removal of the article, and/or f) coordinate with other graphics on the chassis body.

Structural differences and corresponding functional and visual differences between the waist, hip and leg regions 80, 82, 84 of the side panels 30 can be influenced by other components of the diaper. For instance, as described hereunder, elastic waist features and leg elastics can be made to extend into the waist and leg regions of the side panel to enhance the distribution of forces about the wearer as well as provide continuous seams that appear more garment-like.

The diaper 20 may comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 in the second waist region 38 provides an extensible member that provides a more comfortable and contouring fit by initially conformably fitting the diaper to the wearer and sustaining this fit throughout the time of wear well past when the diaper has been loaded with exudates since the extensible waist feature, particularly in the back portion of the diaper allows the diaper to expand and, preferably, to contract. Further, the elastic waist feature 34 in the second waist region 38 develops and maintains wearing forces (tensions) that enhance the tensions developed and maintained by the closure system to maintain the diaper on the wearer and enhance the fit of the diaper 20 about the waist of the wearer. The elastic waist feature 34 in the second waist region 38 further provides more effective application of the diaper 20 since even if the caregiver pulls one side of the elastic waist feature farther than the other during application (asymmetrically), the diaper will "self-adjust" during wear.

The elastic waist feature 34 may be attached to the outer, garment facing surface of the backsheet; the body facing surface of the topsheet or both. In addition the elastic waist feature may be attached between the topsheet and the backsheet, or wrapped around the end edges 52 of the diaper 20 and attached to both the body-facing surface of the topsheet and the garment-facing surface of the backsheet.

The elastic waist feature 34 may be constructed in a number of different configurations. For instance, the elastic waist feature 34 may comprise a laminate structure consisting of a single layer of nonwoven with an elastomeric material attached covering a full width dimension of the nonwoven or only a portion of the width. The elastomeric material may include an elastomer extruded onto the nonwoven or a film that is glued to the nonwoven. Alternatively, the elastic waist feature 34 may comprise a laminate structure comprising two layers of nonwoven with elastomeric strands disposed therebetween covering the full width of the laminate or only a portion of the width. In addition, the elastic waist feature 34 may be constructed according to U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waist cap features such as those described in U.S. Pat. No. 5,026,364 issued to Robertson on Jun. 25, 1991 and U.S. Pat. No. 4,816,025 issued to Foreman on Mar. 28, 1989.

The diaper 20 can also comprise extensible leg cuffs 32 for providing improved containment of liquids and other body exudates. Each extensible leg cuff 32 may comprise several different embodiments for reducing the leakage of body exudates in the leg regions. (The leg cuff can be and is sometimes also referred to as leg bands, leg flaps, barrier cuffs, or elastic cuffs.) The extensible leg cuffs 32 may be attached to the outer, garment facing surface of the backsheet; the body facing surface of the topsheet or both. In addition, the extensible leg cuffs 32 may be attached between the topsheet and the backsheet, or wrapped around the longitudinal side edges 50 of the diaper 20 and attached to both the body-facing surface of the topsheet and the garment-facing surface of the backsheet.

Like the elastic waist feature 34, the extensible leg cuffs 32 may be constructed in a number of different configurations. For instance, the extensible leg cuffs 32 may comprise a laminate structure consisting of a single layer of nonwoven with an elastomeric material attached covering a full width dimension of the nonwoven or only a portion of the width. The elastomeric material may include an extruded elastic strand laminate comprising prestrained extruded elastic strands laminated to a nonwoven or a film that is subsequently glued to the garment facing surface of the backsheet along the longitudinal edges 50 of the diaper 20 and allowed to relax to form a shirred or corrugated structure. Alternatively, the extensible leg cuffs 32 may comprise a laminate structure comprising two layers of nonwoven with prestrained extruded elastic strands laminated between the two layers of nonwoven covering the full width of the laminate or only a portion of the width. The laminate structure can be subsequently glued to the garment facing surface of the backsheet along the longitudinal edges 50 of the diaper 20 while in the prestrained condition so that a shirred or corrugated structure is formed once tension is removed from the laminate allowing it to relax. In addition, the extensible leg cuffs 32 may comprise a prestrained elastic strand or strands bonded in a prestrained condition between a portion of the backsheet or topsheet that is folded over.

In addition, the extensible leg cuffs 32 may be constructed according to one or more of the patents described hereunder. U.S. Pat. No. 3,860,003 entitled "Contractable Side Portions For a Disposable Diaper", issued to Buell on Jan. 14, 1975, describes a disposable diaper providing a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waste Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongations accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks.

Figure 3:
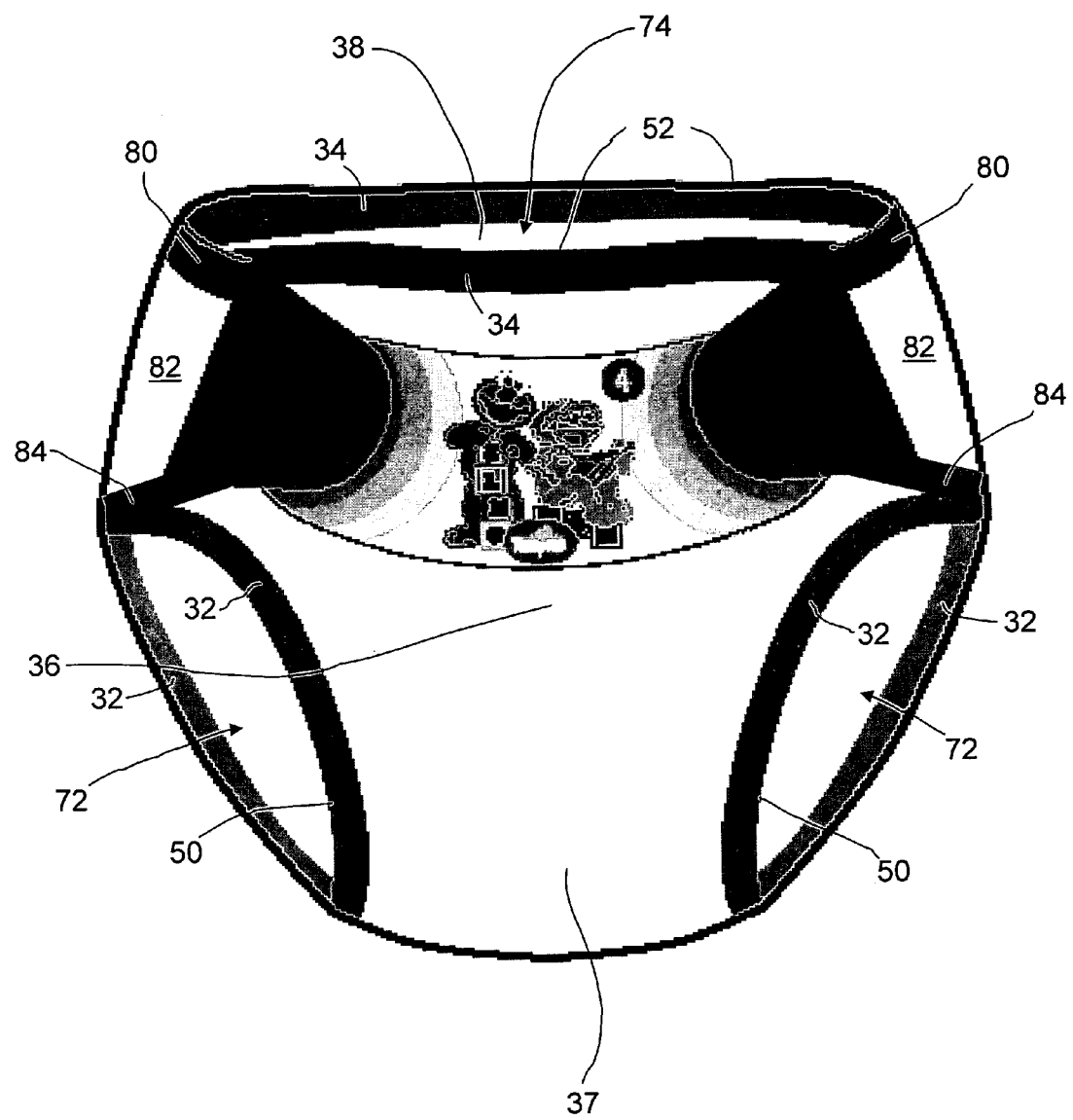
FIG. 3 is an isometric view of the diaper in FIG. 1 configured in a fitted orientation.

FIG. 3 depicts a diaper 20 in a fastened configuration illustrating how visual differences between the waist, hip and leg regions 80, 82, 84 not only exhibit a garment-like look but also provide functional attributes enabling the caregiver to properly align the diaper on the wearer during fitting. As shown, the leg region 84 of the side panel 30 can be made to match the longitudinal edges 50 and the waist region 80 can be made to match the end edges 52 in the first and second waist regions 36, 38. Once the diaper 20 is donned on a wearer, the waist regions 80 of the side panels 30 align with the end edges 52 in the first and second waist regions 36, 38 forming a complete 360° waist band encircling the waist opening 74 of the diaper 20. At the same time, the leg regions 84 of the side panels 30 align with the longitudinal edges 50 of the diaper to form 360° leg bands encircling the leg openings 72.

In addition to visual distinctions, structural differences may be introduced to further enhance the visual features and to provide additional functional attributes of the different regions. For instance, the elastic waist feature 34 in the second waist region 38 can be made to extend into one or both of the side panels 30 partially or fully covering the waist region 80 in one or both of the side panels 30. For the embodiment shown in FIG. 3, the elastic waist feature 34 in the second waist region 38 is shown fully covering the waist region 80 in each of the side panels 30 such that the combination of the elastic waist feature 34 in the second waist region 38 of the diaper and the waist region 80 in each of the side panels 30 aligns with the elastic waist feature 34 in the first waist region 36 of the diaper forming a 360° elastic waist about the waist opening 74 when the diaper 20 is donned on a wearer.

Similarly, the extensible leg cuffs 32 can be made to extend into the leg region 84 of one or both of the side panels 30 partially or fully covering the leg region 84 in one or both of the side panels 30. As shown in FIG. 3, the extensible leg cuffs 32 can be made to fully cover the leg region 84 in each of the side panels 30 such that the combination of the leg region 84 in each of the side panels 30 and the extensible leg cuffs 32 form complete 360° leg elastics about each of the leg openings 72. For this embodiment, the extensible leg cuffs 32 and the leg regions 84 in each of the side panels can include aforementioned visual features to appear as garment-like seams about the leg openings.

For the embodiment illustrated in FIG. 3, the hip region 82 in each of the side panels 30 may comprise a zero-strain elastomeric laminate including an elastic film disposed between two nonwoven layers. The zero-strain elastomeric laminate may terminate at the waist and leg regions 80, 84 or may extend at least partially into the waist and leg regions 80, 84. In the latter case, the waist and leg regions 80, 84 may be disposed on the garment facing side of the zero-strain elastomeric laminate, the body-facing side of the zero strain elastomeric laminate, or both. Alternatively, the waist and leg regions 80, 84 may wrap around the first and second end edges 90, 92, respectively, of the side panels 30 and overlap the zero-strain elastomeric laminate.

Figure 4:
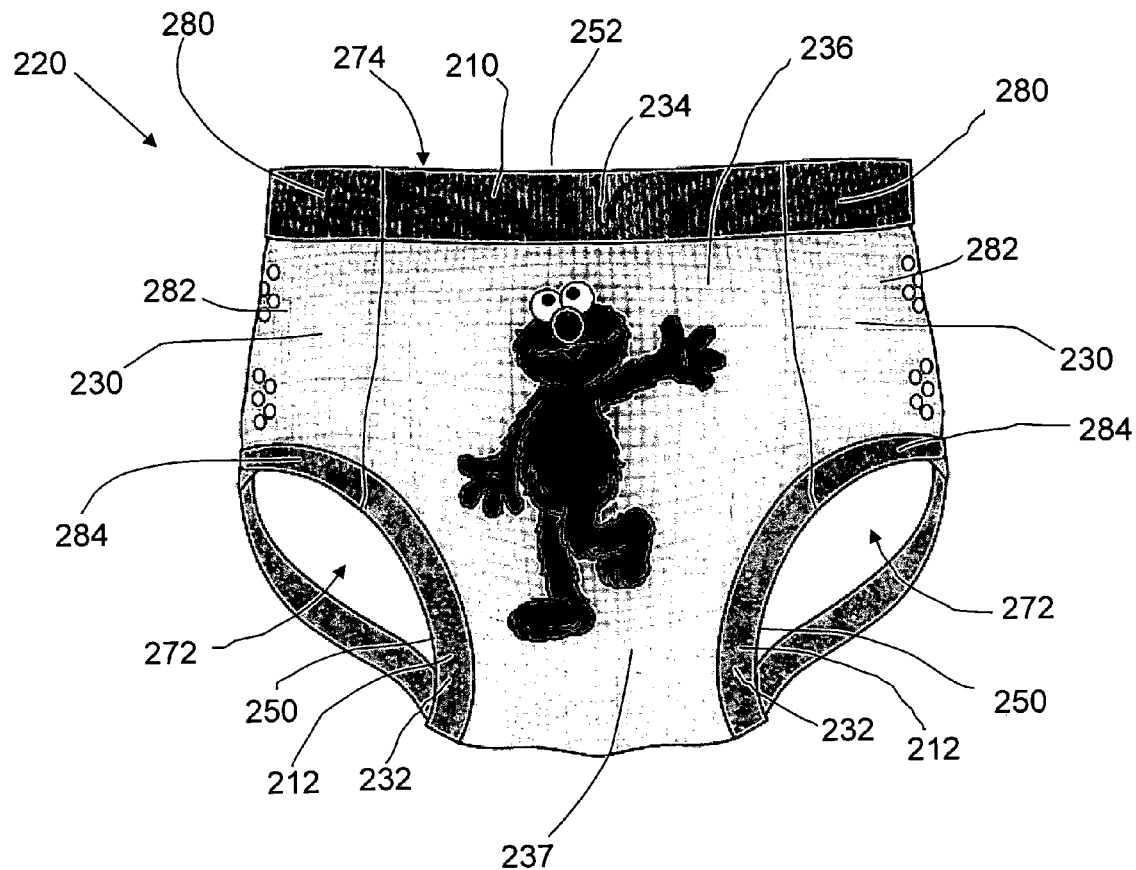
FIG. 4 is an isometric view of a pant style diaper constructed in accordance with the present invention.

FIG. 4 depicts a pant style diaper 220 illustrating how visual distinctions and structural differences between the leg, hip, and leg regions 280, 282, 284 can be made to enhance fit as well as a garment-like look. As shown in FIG. 4, the waist regions 280 of the side panels 230 comprise a continuation of a waist band 210 proximate the end edges 252 in the first waist region 236. The waist band 210 can include an elastic waist feature 234 extending into, and partially or fully covering the waist region 280 in each of the side panels 230. Although not shown, the waist regions 280 of the side panels 230 can also comprise a continuation of a waist band and/or elastic waist feature proximate the end edges in the second waist regions forming, in combination with the elastic waist feature 234 in the first waist region 236, a 360° waist band encircling the waist opening 274. In addition, as shown in FIG. 4, the leg regions 284 of the side panels 230 can comprise a continuation of leg bands 212 proximate the longitudinal edges 250 in the crotch region 237 of the pant style diaper 220 forming 360° leg bands 212 encircling the leg openings 272. The leg bands 212 may also include extensible leg cuffs 232 partially or fully covering the leg regions 284 in each of the side panels 230.

Other components of the chassis 22 include the backsheet 26, the topsheet 24 and the core 28. The backsheet 26 is generally that portion of the diaper 20 positioned adjacent garment facing surface of the absorbent core 28 which prevents the exudates absorbed and contained therein from soiling articles which may contact the diaper 20, such as bed sheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE., and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E.I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets may be made in accordance with U.S. Pat. Nos. 4,609,518 and 4,629,643 issued to Curro et al. on Sep. 2, 1986 and Dec. 16, 1986, respectively. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet 24 is made of a hydrophobic material or is treated to be hydrophobic in order to isolate the wearer's skin from liquids contained in the absorbent core 28. If the topsheet 24 is made of a hydrophobic material, preferably at least a portion of the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and/or immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the topsheet 24 can be found in U.S. Statutory Invention Registration No. H1670 published on Jul. 1, 1997 in the names of Aziz et al. Alternatively, the topsheet 24 may include an apertured web or film which is hydrophobic. This may be accomplished by eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997.

The diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. Pat. No. 6,432,098 entitled "Absorbent Article Fastening Device" in the names of Kline et al. issued on Aug. 13, 2002. The fastening system 40 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987.

Test Methods

Hysteresis Test for Elastic Properties

Overview

This test measures: a) elastic resistance (load at 25% elongation), b) force relaxation, and c) percent set of a side panel region. Ideally, the sample dimension should be 2.54 cm wide×5.08 cm long, with the direction of stretch being the long dimension. Furthermore, ideally, the gage length should be 2.54 cm. Because of the variety of geometries that the regions can be in, it may be necessary to use a different sample width and/or length and normalize the results to the ideal sample basis. Once a sample has been prepared, it is stretched according to a predefined regimen to provide data for property determination.

Apparatus

Tensile Tester: A commercial constant rate of extension tensile tester from Instron Engineering Corp., Canton, Mass. or SINTECH-MTS Systems Corporation, Eden Prairie, Minn. (or a comparable tensile tester) may is suitable. The instrument is interfaced with a computer for controlling the test speed and other test parameters, and for collecting, calculating and reporting the data.

Load Cell Choose the jaws and load cell suitable for the test; the jaws should be wide enough to fit the sample, typically 2.54 cm jaws are used; the load cell is chosen so that the expected tensile response from the sample tested will be between 25% and 75% of the capacity of the load cells or the load range used, typically a 1 kN load cell is used;

Sample Cutter The specific sample cutter is defined by the desired sample width. Suitable cutters are available from Thwing-Albert Instrument Co. of Philadelphia, Pa. For a 2.54 cm wide sample a Model JDC 1-10 is suitable.

Sample Preparation

Cut waist, hip and leg regions from the side panel along the boundary defined by the visible or structural difference. Cut a sample of each region that is 2.54 cm wide by 5.08 cm long from within an individual region. If an individual region is smaller than these dimensions, the sample should comprise the entire region. Orient the sample in the jaws to ensure that the sample is stretched in the longitudinal direction of the region. If the force from an individual region is too small to measure on the tensile tester, several samples from identical region taken from multiple products can be pulled collectively in between the grips of the tensile tester, and the data normalized to an individual region basis.

Method

The hysteresis is measured under standard laboratory conditions (25° C.±2° C. and relative humidity of about 50%±2.0%).

The procedure for determining hysteresis of an elastomeric member involves the following steps:
1. Calibrate the tester according to the manufacturer's instructions.
2. Set the gauge length at 2.54 cm or as appropriate for the sample being tested; set the slack preload at 0.05 N.
3. Place the sample in the flat surface of the jaws such that the longitudinal centerline of the sample is substantially parallel to the gauge length direction.
4. Set the crosshead speed at a constant speed of 25.4 cm/min.
5. Initiate crosshead motion, the tester begins to record load and strain data simultaneously. The hysteresis test specifically involves the following steps:
   a) elongate the sample to 25% strain at a constant rate of 25.4 cm/min-record the force at 25% elongation;
   b) allow the sample to remain at this strain for 2 minutes-record the force at the start and end of the 2 minute period;
   c) return the sample to 0% strain at a constant rate of 25.4 cm/min;
   d) allow sample to remain at this strain for 1 minute; and
   e) elongate the sample to 0.1 N load at a constant rate of 5.08 cm/min-record the strain at 0.1N (i.e., a force sufficient to remove slack but low enough to impart, at most, insubstantial stretch to the sample).

Calculations and Reported Results
1. From the data collected in step 5(a), the load at 25% strain is reported as the elastic resistance of the material.
2. From the data collected in step 5(b), the force relaxation is determined by the load at the beginning and at the end of the 2 minutes hold time using the following formula:

$$\% \text{ Stress Relaxation at time, } t = \frac{[(\text{initial load}) - (\text{load at time, } t)]}{\text{initial load}} \times 100$$

3. From the data collected in step 5(e), the % set is calculated using the following formula:

$$\text{Percent Set} = \left[\left(\frac{\text{Strain Recorded at } 5(e)}{\text{Gage Length}}\right) - 1\right] \times 100$$

4. Report the average results from three replicate samples for each region tested.

Available Strain

Figure 5:
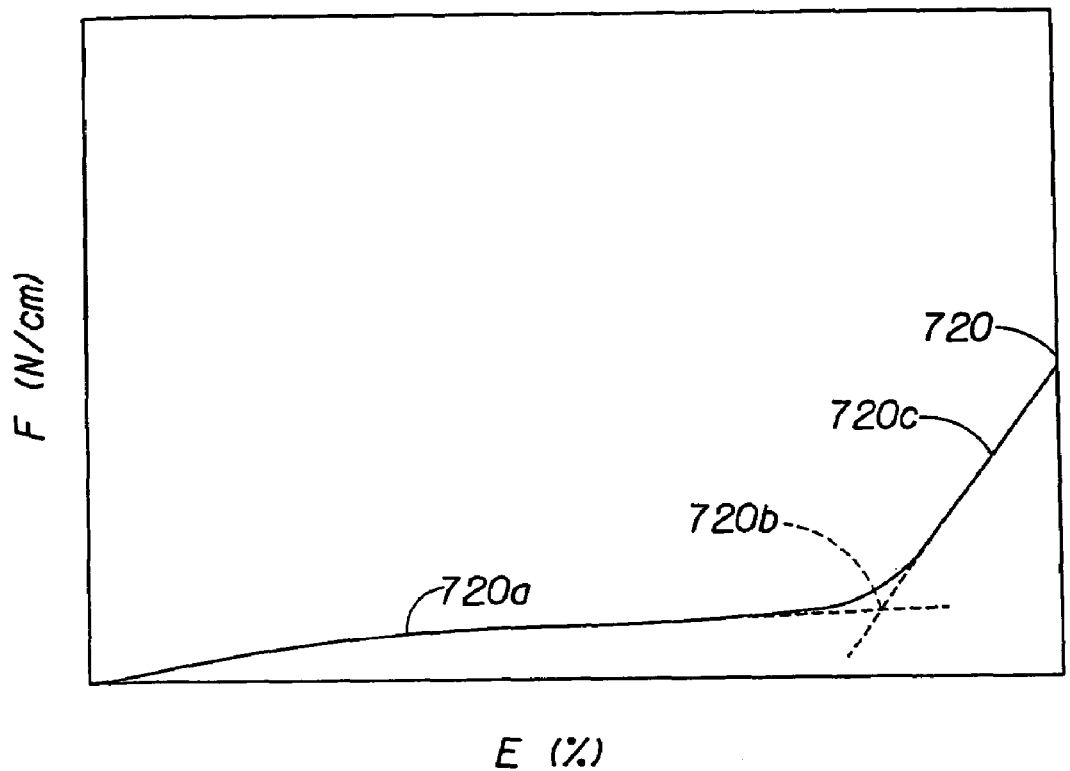
FIG. 5 is an exemplary stress-strain curve showing "Available Strain".

This is intended to determine the Available Strain of a sample. The Available Strain is the point at which there is an inflection in the force—elongation curve, beyond which point there is a rapid increase in the amount of force required to elongate the sample further. An exemplary force (F (N/cm))-elongation (E (%)) curve is shown as FIG. 5. As shown therein, available strain is determined from force elongation curve 720 as the intersection point 720b of linear extrapolations of the stage 1 portion of the curve 720a and the stage 2 portion of the curve 720c.

Method
1. Samples are prepared according to the Hysteresis Test described above.
2. Repeat steps 1-4 of the Hysteresis Test.
3. Initiate crosshead motion. The tester begins to record load versus strain (percent elongation) data simultaneously;
4. Continue elongating the sample until either:
   a) the sample breaks; or
   b) the force limit of the load cell is reached.
5. Plot the force/elongation data to create a curve similar to that shown in FIG. 5.
6. Extrapolate the stage 1 and stage 2 portions as shown to determine the available strain.
7. Report the average results from three replicate samples for each region tested.

All documents cited in the Detailed Description of the Invention are, in relevant part, incorporated herein by reference; the citation of any document is not to be construed as an admission that it is prior art with respect to the present invention. To the extent that any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper to be worn about the lower torso of a wearer, the disposable diaper including an inner body facing surface, an outer garment facing surface, opposing end edges, opposing longitudinal side edges, a first waist region, a second waist region, and a crotch region interposed between the first waist region and the second waist region, the disposable diaper comprising:
   a topsheet;
   a backsheet;
   an absorbent core disposed between the topsheet and the backsheet;
   a pair of side panels, each side panel comprising a first longitudinal edge; a second longitudinal edge opposite the first longitudinal edge; and three regions including a waist region, a hip region and a leg region wherein the first longitudinal edge of each side panel is attached to one of the opposing longitudinal side edges in the second waist region and wherein the waist region, hip region and the leg region differ structurally, functionally or visually;
   a pair of elastically contractible gasketing leg cuffs, disposed adjacent to the opposing longitudinal side edges in the crotch region wherein each of the elastically contractible gasketing leg cuffs extends into the leg region of the corresponding side panel;
   an elastically contractible elastic waist feature disposed in the second waist region adjacent the end edge wherein the elastically contractible elastic waist feature extends into the waist region of each of the side panels;
   a nonelastic extension member attached to the second longitudinal edge of the side panels covering at least a portion of the waist region, the hip region and the leg region; and a fastener joined to the nonelastic extension member, wherein the fastener refastenably attaches to the garment facing surface forming a waist opening and a pair of leg openings.

2. The disposable diaper according to claim 1 wherein the visual differences include colors, textures, patterns, thickness, opacity, reflectivity, sheen, rugosity size, rugosity spacing, and rugosity frequency.

3. The disposable diaper according to claim 1 wherein the structural differences include types of materials, activation patterns, thicknesses, bonding patterns, layers of materials and combinations thereof.

4. The disposable diaper according to claim 1 wherein the functional differences, include stiffness, bending modulus, elastic modulus, extensibility, force relaxation, set, recovery rate, torsional modulus, compression modulus, compressibility, coefficient of friction, surface energy and combinations thereof.

5. The disposable diaper according to claim 1 wherein the waist region and the leg region in each of the side panels are visually, structurally and functionally the same and wherein the leg region and waist region differ structurally, functionally and visually from the hip region.

* * * * *

UNITED STATES PATENT AND TRADEMARK OFFICE
CERTIFICATE OF CORRECTION

PATENT NO. : 7,432,413 B2
APPLICATION NO. : 11/303686
DATED : October 7, 2008
INVENTOR(S) : Donald Carroll Roe et al.

It is certified that error appears in the above-identified patent and that said Letters Patent is hereby corrected as shown below:

<u>Column 16</u>
Line 59, delete ""DR1-WEAVE"" and insert --"DRI-WEAVE"--.

Signed and Sealed this

Fourteenth Day of April, 2009

JOHN DOLL
*Acting Director of the United States Patent and Trademark Office*